4,409,376
Date: Oct. 11, 1983
Inventors: Dowbenko et al.

United States Patent [19]
Dowbenko et al.

[54] NOVEL DILUENTS USEFUL IN PREPARING HIGH SOLIDS COATING COMPOSITIONS

[75] Inventors: Rostyslaw Dowbenko, Gibsonia; Marvis E. Hartman, Pittsburgh; Thomas R. Hockswender, Gibsonia, all of Pa.

[73] Assignee: PPG Industries, Inc., Pittsburgh, Pa.

[21] Appl. No.: 448,168

[22] Filed: Dec. 10, 1982

[51] Int. Cl.³ .................. C08G 8/28; C08L 61/32
[52] U.S. Cl. .................. 525/509; 526/323.2
[58] Field of Search .................. 525/509; 526/323.2

[56] References Cited

U.S. PATENT DOCUMENTS

| | | |
|---|---|---|
| 2,563,133 | 8/1951 | Patrick et al. .................. 260/78.4 |
| 2,759,913 | 8/1956 | Hulse .................. 260/89.7 |
| 3,415,902 | 12/1968 | Hickner et al. .................. 525/509 X |
| 3,959,103 | 5/1976 | Larsen .................. 204/159.19 |
| 4,248,753 | 2/1981 | Buchwalter et al. .................. 260/29.2 TN |
| 4,256,560 | 3/1981 | Buchwalter et al. .................. 204/181 C |
| 4,292,155 | 9/1981 | Bosso et al. .................. 204/181 C |

Primary Examiner—Lucille M. Phynes
Attorney, Agent, or Firm—Godfried R. Akorli

[57] ABSTRACT

There are herein provided reaction products of a compound containing an ethylenically unsaturated group and a compound containing at least two reactive groups of varying reactivity. One of the reactive groups such as a mercapto group reacts through the ethylenically unsaturated group. The resulting products are useful as reactive diluents or as film-formers.

7 Claims, No Drawings

NOVEL DILUENTS USEFUL IN PREPARING HIGH SOLIDS COATING COMPOSITIONS

BACKGROUND OF THE INVENTION

1. Field of the Invention

The present invention relates to coating compositions, particularly high solids coating compositions, comprising diluents.

2. Brief Description of the Prior Art

As is known in the art, one of the aims of coating formulators is to eliminate, or reduce to a minimum, the use of organic solvents as aids to film formation or application. Two distinct approaches to these problems have been used. First, water has been used as the solvent, or carrier, for the polymer; and second, the components of the polymer system have been chosen so that they all—or nearly all—have film-forming potential. In this text, coating systems prepared by the second approach which are generally referred to as high solids systems are of a particular interest.

Some of the advantages of these high solids systems are reduced atmospheric pollution, increased film build with a consequent reduction in volume change and stress development during film formation, simplification of painting operations with respect to the number of coats necessary, and economic gains related to the elimination of volatile expensive solvents.

Elimination of solvents from the coating systems ordinarily causes application problems. To avoid these problems, diluents, particularly reactive diluents, are used in high solids systems to aid the application thereof. By definition, reactive diluents are non-volatile organic liquids which contribute to the viscosity reduction of a coating binder (act as an ordinary solvent) but are also capable of reacting with a crosslinker to become part of a crosslinked coating composition. The extent to which the viscosity is reduced depends on the effectiveness of the diluent.

The present invention provides novel reactive diluents which impart desirable properties to films formed from high solids compositions.

SUMMARY OF THE INVENTION

In accordance with the foregoing, the present invention encompasses a composition of matter comprising a reaction product of:
- (A) a compound containing from about 1 to 4 ethylenically unsaturated groups, and
- (B) a compound having at least two reactive functional groups of varying reactivity; wherein one of said functional groups is a mercapto group which is reactive with the ethylenically unsaturated group or groups of compound (A), and another functional group is a member selected from the group consisting of hydroxyl group, carboxyl group and a group having an oxidizable unsaturation.

The above composition of matter can be added to film-formers in coatings in order to achieve improved application properties. Also, they can be employed in their own right as film-formers.

DETAILED DESCRIPTION OF THE INVENTION

The reaction of compounds (A) and (B) as set forth herein is, preferably, a non-polymerization reaction. Preferably, it is a Michael-addition reaction which involves addition of a nucleophilic compound to another compound through the other compound's ethylenically unsaturated group, i.e., a carbon-carbon double bond which constitutes a Michael acceptor. The resultant reaction product, in accordance with this invention, is of a narrow molecular weight distribution. This is ensured by proper selection of (A) and (B), as is more fully described hereinafter.

Compound (A) contains from about 1 to about 4 ethylenically unsaturated groups; each of the groups, independently, is capable of being a Micheal acceptor in the Michael-addition reaction. Illustrative examples of compound (A) are compounds containing an acrylic group; these are preferred herein. Other examples of compound (A) are compounds containing a vinylic or an allylic group. In accordance with this invention, compound (A) is of a low molecular weight, typically, from about 100 to 2500, and preferably from about 100 to 1000.

A more specific example of the compound containing an acrylic unsaturated group is hydrocarbon or substituted hydrocarbon acrylate. Such a compound can be derived from the reaction of an acrylic acid or methacrylic acid with a polyol. Examples of the polyols are aliphatic diols such as ethylene glycol, 1,2-propanediol, 1,3-propanediol, 2,2,4-trimethyl-1,3-pentanediol, 2,2-dimethyl-1,3-propanediol, 1,2-butanediol, 1,4-butanediol, 1,5-pentanediol and 1,10-decanediol; diols containing a cyclic structure such as 1,4-cyclohexanedimethanol, p-xylylene glycol and 1,4-cyclohexanediol; triols such as glycerol, trimethylolethane, trimethylolpropane and 1,2,6-hexanetriol; tetraols such as pentaerythritol; ether glycols such as diethylene glycol, triethylene glycol, tetraethylene glycol, dipropylene glycol, tripropylene glycol, di-butylene glycol and polyethylene and polypropylene glycols; ester glycols such as 2,2-dimethyl-3-hydroxyproyl 2,2-dimethyl-3-hydroxypropionate; and caprolactone polyols that contain at least 2 hydroxyl groups. The aforementioned acrylic or methacrylic acid is reacted with the polyol is essentially equivalent ratios so as to produce a material of the formula:

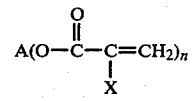

where A is the residue of the hydroxyl-containing material, X is hydrogen or a lower alkyl, preferably, methyl and n is an integer ranging from about 1 to 4. Although n can be an integer higher than 4, compounds corresponding to the higher order of n are not preferred.

Suitable acrylates can be obtained by reacting dicarboxylic acid with hydroxyalkyl acrylates or methacrylates. Yet another method of obtaining the useful acrylates is by reacting the hydroxyacrylates or methacrylates with an excess of caprolactone. Examples of the hdyroxyalkyl acrylates or methacrylates are hydroxyalkyl acrylates and methacrylates wherein the alkyl group contains from 2 to 10 carbon atoms. Examples thereof are 2-hydroxyethyl acrylate, 2-hydroxypropyl acrylate, 3-hydroxypropyl acrylate, 2-hydroxybutyl acrylate, 2-hydroxynonyl acrylate, 2-hydroxyethyl methacrylate and 3-hydroxypropyl methacrylate. Examples of the dicarboxylic acids are maleic acid, adipic acid, sebacic acid, succinic acid, phthalic acid, isophthalic acid and azelaic acid, fumaric acid, citraconic acid and itaconic acid. Anhydrides of the aforementioned acids, where they exist, are intended to be embraced by the term "acid". Examples of the lactones are epsilon-caprolactone, epsilon-methylcaprolactone and butyrolactone.

The resultant reaction product has the formula:

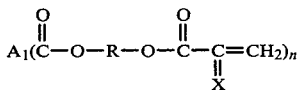

where $A_1$ is the residue of the carboxyl-containing material, R is alkyl group with from 2 to 10 carbon atoms, and X and n are as previously described.

Yet another method of obtaining the acrylates entails reacting an epoxy-containing ethylenically unsaturated monomer such as glycidyl acrylate or methacrylate with a carboxylic acid. Examples of suitable carboxylic acids are the same as those described above.

The resultant reaction product has the formula:

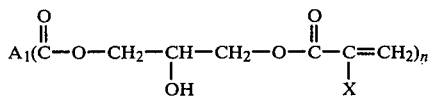

where $A_1$, X and n are as described above.

Another class of compounds containing an acrylic unsaturated group are the low molecular weight urethane acrylates. These compounds are derived from the reaction of an isocyanate with a hydroxyl-containing acrylate or methacrylate. The isocyanate is a di- or polyisocyanate. Several different polyisocyanates are useful. Examples include aliphatic, cycloaliphatic or aromatic compounds having two or more isocyanate groups. Illustrative compounds are 1,4-tetramethylene diisocyanate; 1,6-hexamethylene diisocyanate; 2,2,4-trimethyl-1,6-diisocyanato hexane; 1,10-decamethylene diisocyanate 1,4-cyclohexylene diisocyanate; 4,4'-methylene bis(isocyanato cyclohexane); p-phenylene diisocyanate; isophorone diisocyanate; 2,4-bisphenylene diisocyanate; 4,4'-methylene bis(phenyl isocyanate); 1,5-naphthalene diisocyanate and 1,5-tetrahydronaphthalene diisocyanate. Examples of hydroxyl-containing acrylate and methacrylate compounds reacted with the isocyanate include 2-hydroxyethyl acrylate, 2-hydroxypropyl acrylate, 3-hydroxypropyl acrylate, 2-hydroxyethyl methacrylate, 2-hydroxypropyl methacrylate, 3-hydroxypropyl methacrylate and any of the aforedescribed acrylates which has been modified by reaction with a lactone. Amounts of the hydroxyl-containing acrylate and isocyanate reactants are reacted together. The resultant reaction product has the formula:

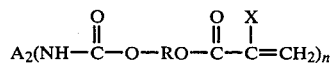

where $A_2$ is the organic residue from the isocyanate, R is a straight or branched chain alkylene group or an ester-containing linkage, X is hydrogen or a lower alkyl, preferably, methyl, and n is at least 2.

Ether acrylates of low molecular weight are useful as compounds containing an acrylic unsaturated group; they are made by different methods. One method involves reacting an ether polyol with acrylic or methacrylic acid. The ether polyols, in turn, are made by reacting a suitable polyol as described above with a monoepoxide such as butyl glycidyl ether, octyl glycidyl ether, allyl glycidyl ether, phenyl glycidyl ether, 1,2-butylene oxide and styrene oxide. Ether acrylates can also be derived from the reaction of (1) an acrylic or methacrylic acid with (2) a polyglycidyl ether of a polyphenol or polyhydric alcohol. Any polyglycidyl ether of a polyphenol or a polyhydric alcohol can be used. Preferred are the polyglycidyl ethers of a polyphenol such as bisphenol A. Other polyglycidyl ethers are obtained by etherification of a polyphenol with epichlorohydrin or dichlorohydrin in the presence of an alkali. The phenolic compound can be 2,2-bis(4-hydroxyphenyl)propane; 4,4'-dihydroxybenzophenone; 1,1-bis(4-hydroxyphenyl)ethane; 2,2-bis(4-hydroxytertiarybutylphenyl)propane and 1,5-dihydroxynaphthalene. Similar polyglydicyl ethers of polyhydric alcohols are derived from such polyhydric alcohols as ethylene glycol, diethylene glycol, triethylene glycol, 1,2-propylene glycol, 1,4-butylene glycol, 1,5-pentanediol and trimethylolpropane. Generally, equivalent amounts of the acrylic or methacrylic acid and polyglycidyl ethers are used.

The resultant reaction product has the formula:

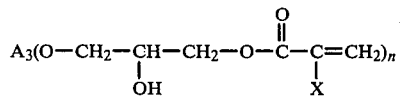

where $A_3$ is the residue of a polyol ether material, X and n are as described above.

Also, the ether acrylates can be made by reacting epoxy-containing ethylenically unsaturated monomers such as glycidyl acrylate or methacrylate with a hydroxy-containing compound such as the polyols described above, in the preparation of hydrocarbon acrylates.

Acrylic acrylates of low molecular weight are also suitable as compounds containing acrylic unsatuniion. One convenient method of making such materials is by reacting (1) a compound containing anhydride groups with (2) a hydroxyl-containing acrylate or methacrylate such as described above. Another method of making the acrylic acrylate class of materials is by reacting a glycidoxy acrylate resin with acrylic or methacrylic acid.

Amide acrylates of low molecular weight are additional classes of compounds containing an acrylic unsaturated group useful herein. One method of obtaining an amide acrylate is by reacting a carboxylic acid, e.g., formic acid with a dialkanolamine and then reacting that product with acrylic or methacrylic acid. Adjusting the relative amounts of the reactants may be necessary to insure free carboxyl groups, but no amino groups.

Compounds of low molecular weight containing an allylic unsaturated group generally correspond to the above-described classes of acrylic compounds, with the acrylic radical of the product replaced by an allylic radical. Ester allylates can be made by reacting an excess of dicarboxylic acid with a polyol and then reacting this product with allyl alcohol. Reacting an excess of caprolactone with allyl alcohol also results in an ester allylate. Urethane allylates are made by reacting a polyisocyanate with allyl alcohol. Amide allylates are obtained by reacting a polyamine having amido hydrogens with allyl alcohol. Acrylic allylates are obtained by reacting acrylic anhydride with allyl alcohol. The individual reactants which are used are exemplified above in regard to the description of the various acrylates.

Similarly, compounds of low molecular weight containing a vinylic unsaturated group generally correspond to the above-described classes of acrylic compounds, with the acrylate radical replaced with a vinylic radical.

Compound (B) has at least two reactive functional groups of varying reactivity. One of the reactive functional groups is a mercapto group which Michael-adds to the ethylenically unsaturated group of compound (A), described above. The other functional group is a member selected from the group consisting of hydroxyl group, carboxyl group and other groups that do not compete with the Michael addition reaction of the mercapto group, for example, oxidizable unsaturation. Illustrative examples of these compounds are mercaptoethanol, mercaptopropanol, alpha-mercaptopropionic acid, thioglycerol, beta-mercaptopropionic acid and fatty mercaptans such as 2-mercaptoethyl laurate and 2-mercaptoethyl stearate. Mercaptoethanol is preferred. In accordance with this invention, compound (B) is of molecular weight typically from about 75 to 500, and preferably from about 78 to 200.

The reaction conditions for the preparation of the compositions of matter of this invention are as follows. The compound containing the ethylenic unsaturation is reacted with the compound containing the reactive functional groups either in the presence or in the absence of a solvent. The solvents useful herein can be non-reactive solvents such as ketones, esters, hydrocarbons, and the like. The reaction is usually exothermic, but it may be carried out at temperatures ranging from 15° to 150° C. Catalysts such as sodium methoxide or other strong bases such as potassium hydroxide can be used in carrying out the reaction.

The equivalent ratio of the compound containing the ethylenic unsaturation to the compound conataining the reactive functional groups is in the range of 1:0.5, preferably 1:0.8, and more preferably 1:1. The resultant composition of matter is formed via the Michael addition reaction of the mercapto functional group with the ethylenic unsaturation.

In a specific embodiment of the invention, a single molecular species such as hexanediol diacrylate or 2,2-dimethyl-3-hydroxypropyl 2,2-dimethyl-3-hydroxypropionate diacrylate is reacted with 2 moles of mercaptoethanol. The resultant composition is a single molecular species. Unlike many art-known compositions useful as reactive diluents, the compositions of this embodiment of the invention are free of relatively low and relatively high molecular species.

In the practice of the invention, the instant composition can be used as a diluent per se, in a coating composition. As diluents, the instant composition can be employed in combination with film formers, and crosslinking agents. The film-formers can comprise an epoxy resin, an acrylic resin, a polyurethane resin, a polyester resin or the like. The crosslinking agent can be an isocyanate or an aminoplast or the like. Alternately, the instant composition can be used as a film-forming composition. Typically, the diluent comprises from about 10 to 80, and preferably from about 15 to 40 percent by weight, based on the total weight of the coating composition. The coating composition can contain coating ingredients such as pigments, fillers, plasticizers, antioxidants, flow control agents, surfactants and the like.

The coating compositions herein can be applied by conventional coating methods such as brushing, dipping, flow coating, roll coating and spraying. Virtually any substrate, for example, wood, metals, glass and plastics can be coated with the compositions.

These and other aspects of the invention are illustrated by the following non-limiting examples.

EXAMPLE I

This example illustrates the preparation of the instant compositions of matter. The following were used in the preparation.

| Ingredients | Parts by Weight (grams) |
|---|---|
| Mercaptoethanol | 150 |
| 1,6-Hexanediol diacrylate | 230 |
| Sodium methoxide (catalyst) | 0.5 |

The mercaptoethanol and sodium methoxide were charged to a properly equipped reaction vessel at 26° C., followed by addition of the 1,6-hexanediol diacrylate. There was a resulting exotherm; the temperature of the resulting mixture was held at 120° C. until the addition of the 1,6-hexanediol diacrylate was completed. Upon completion of the addition, the resulting mixture was held for about 2 ½ hours over a temperature range of 88° to 112° C. and then cooled. The resulting product had a solids content of 98.72, viscosity of G-H, hydroxyl number of 238 and mercapto equivalent of infinity.

EXAMPLE II

This example illustrates the use of the instant compositions in combination with melamine curing agents.

Twenty-five grams of the composition of matter which was prepared as described in Example I was blended with 25 grams of CYMEL 303 (melamine-formaldehyde curing agent available from American Cyanamid Company) and one milliliter of CAT 1010 (10% solution of p-toluene sulfonic acid, available from American Cyanamid Company). The resulting mixture was drawn down on a steel substrate to produce films of 3-mil thickness. The substrates were baked for 30 minutes at 250° F. (121° C.) to produce cured films, in that it took 50 acetone double rubs to remove them.

EXAMPLE III

This example illustrates the preparation of the reactive diluents of the present invention.

| Ingredients | Parts by Weight (grams) |
|---|---|
| 2-Mercaptoethanol | 93.6 |
| Sodium methoxide | 2.0 |
| ESTER DIOL 204 diacrylate[1] | 207.6 |
| 30% Hydrogen peroxide | 1.5 |

[1] 2,2-dimethyl-3-hydroxypropyl 2,2-dimethyl-3-hydroxypropionate diacrylate.

To a properly equipped reaction vessel (under a nitrogen blanket) was charged the 2-mercaptoethanol and sodium methoxide at 87° C., followed by addition of the ESTER DIOL 204 diacrylate. There resulted an exotherm; the temperature of the reaction mixture was kept under 120° C. until the addition of the ESTER DIOL was completed. Thereafter, the reaction mixture was cooled to about 100° C., followed by addition of the hydrogen peroxide to reduce the odor of the resultant product. There resulted an exotherm; the reaction temperature was kept at 100° C. for three hours.

The resultant product had a solids content of 95.9 percent at 105° C., a viscosity of 3.6 stokes, a hydroxyl value of 229.2 and an acid number of 14.

EXAMPLE IV

This example illustrates the effect of the instant compositions in their use as diluents in high solids compositions.

A high solids composition was prepared, blended with the diluent in different proportions, and evaluated as follows.

The following were used in preparing the high solids composition.

Composition A

| Ingredients | Parts by Weight (grams) |
| --- | --- |
| AT 400[1] | 75 |
| CYMEL 303[2] | 40 |
| Methyl amyl ketone | 40 |
| CAT 4040[3] | 1.2 |

[1] High solids acrylic resinous composition, available from Rohm and Haas Company.
[2] Melamine-formaldehyde crosslinking agent, available from American Cyanamid Company.
[3] 40% p-toluene sulfonic acid solution, available from American Cyanamid Company.

The above ingredients were blended at ambient temperature.

Composition B

A high solids composition, which was essentially the same as Composition A, was blended with a diluent which was prepared in essentially the same manner as described in Example III.

The following were used in the preparation:

| Ingredients | Parts by Weight (grams) |
| --- | --- |
| AT 400 | 50 |
| Composition of Example III (diluent) | 15 |
| CYMEL 303 | 40 |
| Methyl amyl ketone | 32 |
| CAT 4040 | 1.2 |

Composition C

A high solids composition was prepared in the same manner as described in the preparation of Composition A.

The following were used in the preparation:

| Ingredients | Parts by Weight (grams) |
| --- | --- |
| AT 400 | 37.5 |
| Composition of Example III (diluent) | 30 |
| CYMEL 303 | 40 |
| Methyl amyl ketone | 25 |
| CAT 4040 | 1.2 |

Composition D

This example illustrates the use of the compositions of this invention as film-formers in coating compositions.

The following were used in the preparation of the coating composition.

| Ingredients | Parts by Weight (grams) |
| --- | --- |
| Composition of Example III (film-former) | 60 |
| CYMEL 303 | 40 |
| Methyl amyl ketone | 13 |
| CAT 4040 | 1.2 |

EXAMPLE V

Evaluation: The compositions of Example IV were evaluated for solution properties. They were also evaluated for film properties after they had been drawn down on panels of steel substrate and baked at 250° F. (121° C.) for 30 minutes to form films of 3-mil thickness. The results of the evaluation were as reported below.

| Coating Composition | Viscosity #4 Ford Cup, in seconds | Percent Theoretical Solids | Volatile* Organic Content | Sward Hardness | Acetone Rubs | Mandrel Bend |
| --- | --- | --- | --- | --- | --- | --- |
| Composition A | 34 | 64.5 | 3.65 | 36 | 50+ | Fail |
| Composition B | 36 | 69.9 | 3.31 | 36 | 50+ | Pass |
| Composition C | 36 | 75.2 | 3.02 | 30 | 50+ | Pass |
| Composition D | 36 | 88.5 | 2.29 | 6 | 50+ | Pass |

*Pounds of organic volatile per gallon of the coating composition.

The above descriptions and specific illustrations are not intended to limit the invention. Instead, it is intended that the invention include all the variations and modifications falling within the scope of the appended claims.

Therefore, what is claimed is:

1. A composition of matter, comprising a reaction product of:
   (A) a compound containing from about 1 to 4 ethylenically unsaturated groups, and
   (B) a compound having at least two reactive functional groups of varying reactivity; wherein one of said functional groups is a mercapto group which is reactive with the ethylenically unsaturated group or groups of compound (A), and another functional group is a member selected from the group consisting of hydroxyl group, carboxyl group and a group having an oxidizable unsaturation.

2. A composition of claim 1, wherein the ethylenically unsaturated group of compound (A) is vinylic, allylic or acrylic.

3. A composition of claim 2, wherein compound (A) contains 1 to 4 ethylenically unsaturated groups selected from acrylamide, methacrylamide, acrylate or methacrylate.

4. A composition of claim 1, wherein the other functional group is a hydroxyl group.

5. A composition of matter comprising the reaction product of:
   (A) 1,6-hexanediol diacrylate or 2,2-dimethyl-3-hydroxypropyl 2,2-dimethyl-3-hydroxypropionate diacrylate, and
   (B) mercaptoethanol or mercaptopropanol.

6. A coating composition comprising:
   (i) the composition of claim 1, and
   (ii) a crosslinking agent which is an isocyanate or an aminoplast.

7. A high solids composition comprising the composition of claim 1.

* * * * *